United States Patent [19]

Witte

[11] 4,054,391
[45] Oct. 18, 1977

[54] SPECULAR REFLECTANCE MICRODENSITOMETER

[75] Inventor: John C. Witte, Rochester, N.Y.

[73] Assignee: Xerox Corporation, Stamford, Conn.

[21] Appl. No.: 642,101

[22] Filed: Dec. 18, 1975

[51] Int. Cl.² .......................................... G01N 21/48
[52] U.S. Cl. ................................................ 356/209
[58] Field of Search ............... 356/209, 210, 211, 212

[56] References Cited

U.S. PATENT DOCUMENTS

| 2,164,513 | 7/1939 | Gaebel | 356/209 |
| 3,245,306 | 4/1966 | Potter et al. | 356/209 |
| 3,421,806 | 1/1969 | Weber | 356/201 |

*Primary Examiner*—Vincent P. McGraw
*Attorney, Agent, or Firm*—Robert J. Bird

[57] ABSTRACT

A specular reflectance microdensitometer including an illuminating microscope and a collecting microscope, disposed on optical axes at equal and opposite angles relative to a reflecting test surface. The illuminating microscope illuminates a known area on the test surface from which light is reflected into the collecting microscope. The objective lens of the collecting microscope images the illuminated test surface on a field lens which in turn images the objective lens on the face of a fiber optic bundle. The light incident on the fiber bundle is transmitted to a photomultiplier tube for quantitative determination of light level.

The amount of light specularly reflected by the test surface is correlated to the density of particle coverage on the surface, and plotted on an X-Y record.

3 Claims, 2 Drawing Figures

SPECULAR REFLECTANCE MICRODENSITOMETER

BACKGROUND OF THE INVENTION

This invention relates to densitometers, and more particularly to a specular reflectance microdensitometer for measuring and controlling the density of particles on a reflective surface.

One environment for use of such an instrument is in the field of xerography in which electroscopic toner particles are electrostatically applied imagewise to a photoconductive surface from which they are transferred to a support surface such as paper on which they are permanently fixed. For the sake of quality control it is desirable to monitor and control the amount of toner deposited on a xerographic surface prior to its transfer to a final support.

Reference is hereby made to U.S. Pat. No. 3,348,523, issued to Davidson and Pierce, the specification of which is incorporated herein by reference. The cited patent discloses a sensing device in a xerographic environment in the form of a photocell provided for receiving light rays reflected from a developed xerographic image. The light sensing device generates a signal in accordance with the relative density of the developed xerographic image and an associated electrical circuit provides feedback from the generated signal into the system to control the deposition of toner onto the surface.

It is an object of the invention to provide a specular reflection densitometer in which there is a substantially linear relationship between surface density and the output signal of the instrument.

SUMMARY OF THE INVENTION

The present invention is practiced in one form by an illuminating microscope disposed relative to a test surface to illuminate the same over a controlled area, combined with a collecting microscope receiving specular reflection from the illuminated area of the test surface. The collecting microscope images the illuminated test area by means of an objective lens onto a field lens, the field lens in turn imaging the light pupil of the objective lens onto the face of a fiber optic bundle which is operatively connected to a photomultiplier tube for quantitative determination of light level. The optical signal to the photomultiplier is proportional to the amount of the test surface at any instant in the field of view of the instrument, which is not obscured by toner.

For a better understanding of this invention, reference is made to the following detailed description of an exemplary embodiment, given in connection with the accompanying drawing.

DRAWING

DESCRIPTION

Figure 1:
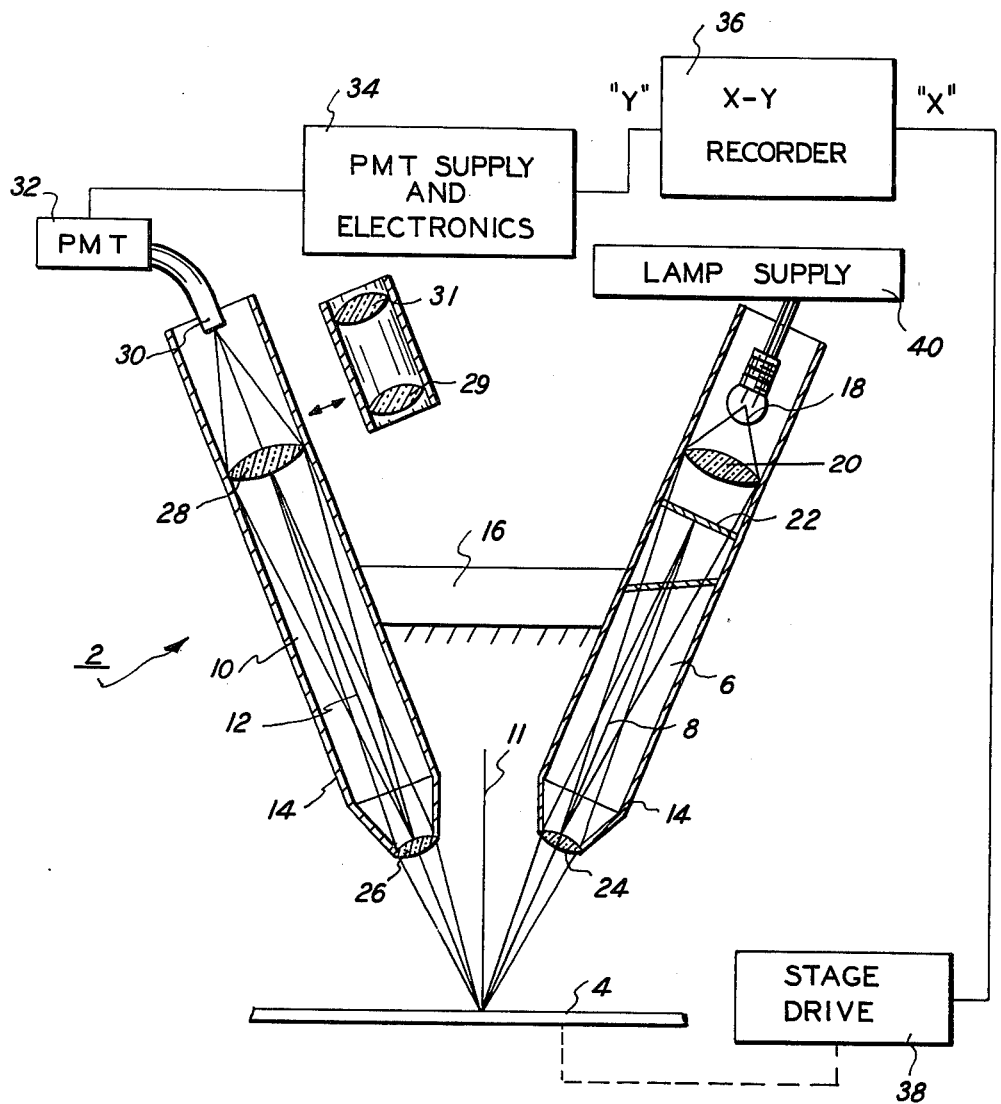
FIG. 1 is a schematic diagram of the optical system and associated components of this invention.

Referring now to FIG. 1, a specular reflectance microdensitometer is indicated generally at 2 and is shown in operative position relative to a specularly reflective test surface 4. Densitometer 2 includes an illuminating microscope 6 disposed along an illumination optical axis 8 relative to the test surface 4, and a collecting microscope 10 disposed along a reflection optical axis 12 relative to the test surface 4. Microscopes 6 and 10 are suitably mounted in microscope tubes 14 to a frame which is schematically represented at 16. Optical axes 8 and 12 are disposed at equal and opposite angles to the normal to test surface 4, represented at 11.

Illuminating microscope 6 includes a light source 18, a condenser lens 20, a slit aperture 22, and an objective lens 24, all disposed along the illumination optical axis 8. Similarly, the collecting microscope 10 includes an objective lens 26, a field lens 28, and a fiber optic probe all disposed along the optical axis 12.

The fiber optic probe 30 is operatively connected to a photomultiplier tube 32 which is in turn operatively connected to an appropriate power supply 34, and X-Y recorder 36, and a drive means 38 by which to effect relative movement between densitometer 2 and the test surface 4. A suitable power supply 40 is connected to the light source 18.

A focusing eyepiece comprising a field lens 29 and an ocular 31 is disposed relative to the collecting microscope 10 for positioning into and out of the optical axis interchangeable with the field lens 28 and the fiber optic probe 30.

In the illuminating microscope, light source 18 and objective lens 24 are in conjugate relationship relative to condenser lens 20 so that light source 18 is imaged on objective lens 24. Slit aperture 22 and test surface 4 are in conjugate relationship relative to objective lens 24 so that the aperture 22 is imaged on the test surface 4. Aperture 22 is a longitudinal slit extending in the direction normal to the paper so that it is in focus on surface 4 along its entire length.

In the collecting microscope, the test surface 4 and the field lens 28 are in conjugate relationship relative to the objective lens 26 so that the illuminated slit on surface 4 is imaged on the field lens 28. Objective lens 26 and the end face of the fiber optic probe 30 are in conjugate relationship relative to the field lens 28 so that the lens 26, the pupil of the system, is imaged on the face of the fiber bundle.

Figure 2:
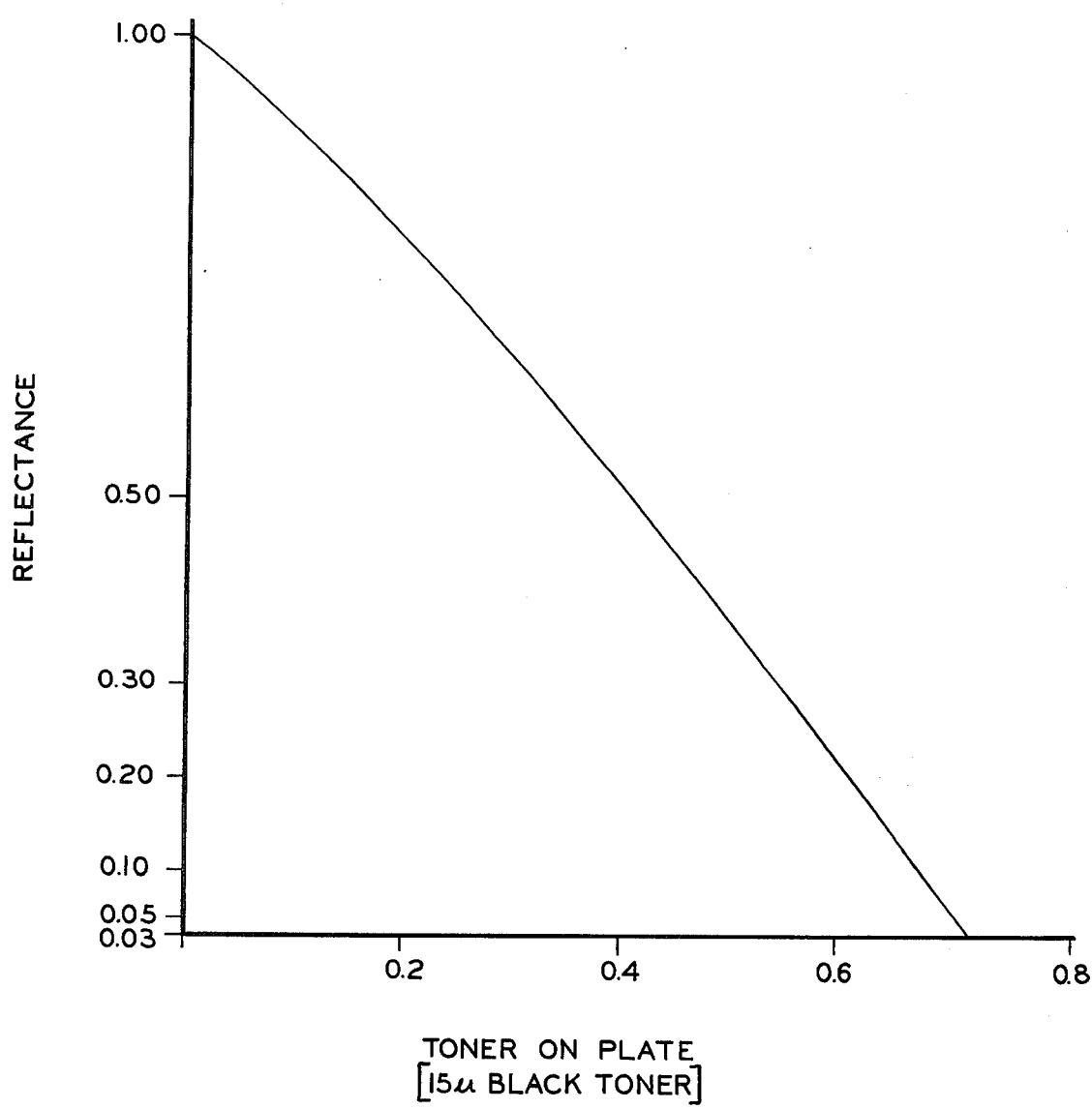
FIG. 2 is a curve of reflectance versus test surface density as measured by the instrument of this invention.

The reflectance of a clean photoreceptor is by convention denoted as unit reflectance. The reflectance as determined by the plate microdensitometer of a photoreceptor partially covered by toner is the ratio of the amount of light reflected into the collecting microscope by the partially toned plate to the amount of light so reflected by a clean photoreceptor. This ratio is denoted R. Optical density is defined as $D = -\log_{10} R$. Theoretical considerations lead one to predict that, under conditions where individual, substantially black, toner particles are deposited at random on the photoreceptor to some mean level determined by the circumstances of deposition, the optical density of an area, large compared to the size of an individual toner particle, will be strictly proportional to the mass of toner deposited. It is of interest to note that the empirically observed response of the microdensitometer has the measured optical density approximately linearly proportional to the mass of toner on the photoreceptor. FIG. 2 shows reflectance plotted on a logarithmic scale to achieve approximate linearity with the mass of toner on the plate expressed as milligrams per square centimeter.

In operation, the illuminating microscope 6 illuminates and images the slit aperture 22 on the test surface 4. Light incident on the test surface 4 from the illuminating microscope specularly reflects into the collecting microscope 10, since the two are mounted at equal and opposite angles relative to the surface 4. If the surface 4 has no particle coverage and is 100% reflective, a clear field is imaged at the field lens and thus light from the object lens is imaged without attenuation on the face of the fiber probe 30. Similarly, a test surface area 4 with 100% particle coverage and not reflective of light produces no light at the fiber optic end surface. Between these extremes, a test surface area partly covered with particles is imaged at field lens 28 and this imaged particle array on the lens 28 attenuates light passing therethrough in proportion to the percent of area coverage of the surface 4 (and of its image in lens 28). This effects a correspondingly attenuated light signal from the fiber probe to the associated photomultiplier tube.

Photomultiplier tube 32 relays its signal to an X-Y recorder 36 which in turn is connected to the drive means 38 so that the X-Y recorder plots a continuous curve of reflectance on a vertical scale corresponding to the lateral position of the test surface 4 on the horizontal scale.

FIG. 2 shows the relationship between the light signal provided to the photomultiplier tube 32 from the reflectance from test surface 4, as a function of particle coverage of the surface. The relationship is a linear one and the curve is substantially linear attesting to the validlity of the technique of this invention.

The curve is exemplary and is specific for one size of toner particle as indicated. Other types of toner would show other curves, but they would still be substantially linear. Only the slope of the curve would be different.

In some instances, particularly where test surface 4 is a photoconductive material, it may be desirable to avoid exposing the surface to light to which it is photosensitive. One technique is to use light of a wavelength which is absorbed by the photoconductor, and therefore does not contribute to photoconductivity, and to observe the reflection from the substrate rather than from the surface. This technique might be used where surface detail is not important. In the case of amorphous selenium again, infrared light may be used for this technique.

The foregoing description of an embodiment of this invention is given by way of illustration and not of limitation. The concept and scope of the invention are limited only by the following claims and equivalents thereof which may occur to others skilled in the art.

What is claimed is:

1. A microdensitometer for measuring and recording relative reflectance of a specularly reflecting surface, including:
    an illuminating microscope disposed on an illumination optical axis relative to said reflecting surface and including a light source, a condensor lens, an aperture and a first objective lens in optical alignment along said illumination optical axis, said light source and said first objective lens being in conjugate relationship to said condenser lens, said aperture and said reflecting surface being in conjugate relationship relative to said first objective lens,
    A collecting microscope disposed on a reflection optical axis to said reflecting surface and including a second objective lens, a field lens, and an optical probe in optical alignment along said reflection optical axis, said reflecting surface and said field lens being in conjugate relationship relative to said second objective lens, said second objective lens and said optical probe being in conjugate relationship relative to said field lens,
    said illumination and reflection optical axes being disposed at equal and opposite angles relative to said reflecting surface,
    whereby an image of said reflecting surface is projected to said field lens to attenuate the light transmission of said field lens in proportion to the extent of particle coverage of said reflective surface.

2. A microdensitometer as defined in claim 1 further including a focusing eyepiece selectively positionable into and out of said reflection optical axis to focus said illumination and said collecting microscope relative to said reflective surface.

3. A microdensitometer as defined in claim 1
    further including a photosensitive element to sense light incident on said optical probe,
    a drive means to effect relative movement between said reflective surface and said microdensitometer,
    a recorder operatively connected to said photosensitive element and to said drive means to concurrently record intensity signals from said photosensitive element and position signals from said drive means.

* * * * *